United States Patent
Graf et al.

(10) Patent No.: US 9,857,381 B2
(45) Date of Patent: *Jan. 2, 2018

(54) METHOD FOR ASSAYING SEPSIS IN HUMANS

(71) Applicant: UNIVERSITAET ZUERICH, Zurich (CH)

(72) Inventors: Rolf Graf, Zurich (CH); Daniel Bimmler, Kuesnacht (CH); Marius Keel, Zurich (CH)

(73) Assignee: UNIVERSITAET ZUERICH, Zurich (CH)

(*) Notice: Subject to any disclaimer, the term of this patent is extended or adjusted under 35 U.S.C. 154(b) by 673 days.

This patent is subject to a terminal disclaimer.

(21) Appl. No.: 13/853,514

(22) Filed: Mar. 29, 2013

(65) Prior Publication Data

US 2013/0203612 A1 Aug. 8, 2013

Related U.S. Application Data

(63) Continuation of application No. 12/676,650, filed as application No. PCT/EP2008/007158 on Sep. 2, 2008, now Pat. No. 8,435,755.

(30) Foreign Application Priority Data

Sep. 7, 2007 (EP) .................................. 07017539

(51) Int. Cl.
*G01N 33/68* (2006.01)

(52) U.S. Cl.
CPC ... *G01N 33/6893* (2013.01); *G01N 2333/474* (2013.01); *G01N 2800/26* (2013.01)

(58) Field of Classification Search
None
See application file for complete search history.

(56) References Cited

U.S. PATENT DOCUMENTS

| | | |
|---|---|---|
| 2004/0265230 A1 | 12/2004 | Martinez et al. |
| 2005/0059104 A1 | 3/2005 | Bergmann |
| 2005/0064506 A1 | 3/2005 | Bergmann |
| 2005/0074811 A1 | 4/2005 | Bergmann |
| 2005/0106645 A1 | 5/2005 | Bergmann |
| 2007/0224638 A1 | 9/2007 | Melanitou-Mcclymont |
| 2013/0079296 A1* | 3/2013 | Stolz .................. G01N 33/6893 514/42 |

FOREIGN PATENT DOCUMENTS

| | | |
|---|---|---|
| WO | 90/06993 A1 | 6/1990 |
| WO | 98/00561 A1 | 1/1998 |
| WO | 2004/087874 A | 10/2004 |

OTHER PUBLICATIONS

Bimmler et al. "Regulation of PSP/reg in rat pancreas: immediate and steady-state adaptation to different diets", Pancreas Oct. 1999;19(3):255-67.*

American College of Chest Physicians/Society of Critical Care Medicine Consensus Conference: Definitions for sepsis and organ failure and guidelines for the use of innovative therapies in sepsis. Crit Care Med 1992; 20:864-874.*

Mayeux et al. "Biomarkers: Potential uses and Limitations"; NeuroRx (2004); vol. 1, pp. 182-188.*

Fujishiro et al. "Regenerating gene (REG) 1 alpha promotes pannus progression in patients with rheumatoid arthritis" Mod Rheumatol. Apr. 2012;22(2):228-37. doi: 10.1007/s10165-011-0564-y. Epub Dec. 28, 2011.*

Nakae et al. "Molecular Forms of Serum Pancreatic Stone Protein in Acute Pancreatitis" International Journal of Pancreatology, vol. 25, No. 1, Feb. 17-21, 1999.*

LaBaer et al. Journal of Proteome Research 2005, 4, 1053-1059.*

Planes et al. "Regenerating gene Ia is a biomarker for diagnosis and monitoring of celiac disease: a preliminary study" Transl Res. Sep. 2011;158(3):140-5. doi: 10.1016/j.trsl.2011.04.004. Epub May 30, 2011, doi:10.1016/j.trsl.2011.04.004.*

Yoshino N. et al.: "Interleukin-8 regulates expression of Reg protein in Helicobacter pylori-infected gastric mucosa" in Am. J. Gastroenterol., vol. 100, No. 10, Oct. 2005, pp. 2157-2166

Graf R. et al.: "Coordinate Regulation of Secretory Stress Proteins (PSP/reg, PAP I, PAP II, and PAP III) in the Rat Exocrine Pancreas during Experimental Acute Pancreatitis" in J of Surg Res, vol. 105, No. 2, Jun. 15, 2002, pp. 136-144.

Kinoshita Y. et al.: "Reg Protein is a Unique Growth Factor of Gastric Mucosal Cells" in J. Gastroenterology 2004, vol. 39, 2004, pp. 507-513.

Satomura et al., "Measurement of Serum PSP/reg-Protein Concentration in Various Diseases with a Newly Developed Enzyme-Linked Immunosorbent Assay," in J Gastroenterology 1995, vol. 30, 1995, pp. 643-650.

Bone et al., Definitions for Sepsis and Organ Failure and Guidelines for the Use of Innovative Therapies in Sepsis. Chest 1992;101 ;1644-1655.

Angus & Wax, Epidemiology of sepsis an update. Crit. Care Med 2001 vol. 29, No. 7. 109-116.

Riedemann et al., The enigma of sepsis. J. Clin. Invest. 112:460-467 (2003).

Trzeciak et al., Inclusion Criteria for Clinical Trials in Sepsis. Chest 2005; 127:242-245.

Lever & MacKenzie. Sepsis definition, epidemiology, and diagnosis. BMJ (Oct. 27, 2007) vol. 335:879-883.

Nguyen & Smith, Sepsis in the 21st century recent definitions and therapeutic advances. American Journal of Emergency Medicine (2007) 25, 564-571.

Vincent et al., Evolving concepts in sepsis definitions. Crit Care CLin 25 (2009) 665-675.

(Continued)

*Primary Examiner* — Christine Foster
(74) *Attorney, Agent, or Firm* — Agris & Von Natzmer, LLP; Joyce Von Natzmer

(57) ABSTRACT

The present invention relates to a reliable method of prediction of sepsis in humans after a trauma, wherein the level of pancreatic stone protein/regenerating protein (PSP/reg) is determined in serum, and a high level is indicative of the development of sepsis at early stages of the disease. Furthermore a method of determination of PSP/reg levels in serum is described.

12 Claims, 6 Drawing Sheets

(56) References Cited

OTHER PUBLICATIONS

Ognibene et al., Depressed Left Ventricular Performance; Response to Volume Infusion in Patients with Sepsis and Septic Shock Chest 93.5. May 1988, vol. 93, No. 5, pp. 903-910.

Hack et al., Increased Plasma Levels of Interleukin-6 in Sepsis. Blood, vol. 74, No. 5 Oct. 1989 pp. 1704-1710.

Fingerie et al., The Novel Subset of CD14+/CD16+ Blood Monocytes Is expanded in Sepsis Patients. Blood, vol. 82, No. 10 Nov. 15, 1993 pp. 3170-3176.

McCall et al., Tolerance to Endotoxin-induced Expression of the Interleukin-113 Gene in Blood Neutrophils of Humans with the Sepsis Syndrome. J. Clin. Invest. vol. 91, Mar. 1993, 853-861.

Kobold et al., Levels of soluble FcyRIII correlate with disease severity in sepsis. Clin Exp Immunol 1998; 114:220-227.

Bernard et al., Efficacy and Safety of Recombinant Human Activated Protein C for Severe Sepsis. N Engl J Med. Mar. 8, 2001; 344(10):699-709.

Levy et al., 2001 SCCM/ESICM/ACCP/ATS/SIS International Sepsis Definitions Conference. Intensive Care Med (2003) 29:530-538.

Vincent, Dear SIRS I'm sorry to say that I don't like you . . . Crit.Care Med. 1997 vol. 25. No. 2 pp. 372-374.

Weiss et al., Different patient case mix by applying the 2003 SCCM/ESICM/ACCP/ATS/SIS sepsis definitions instead of the 1992 ACCP/SCCM sepsis definitions in surgical patients a retrospective observational study. BMC Medical Informatics and Decision Making 2009, 9:25. p. 1-9.

Graf et al., Exocrine Meets Endocrine Pancreatic Stone Protein and Regenerating Protein—Two Sides of the same Coin. Journal of Surgical, 133, 113-120 (2006).

Claims found allowable by the European Patent Office in the Proceeding for EP2185937 (dated May 29, 2010), (one page).

Decision to grant a European patent pursuant to Article 97(1) EPC (dated Jun. 6, 2011), (two pages).

Opposition against patent EP2185937 (dated Mar. 29, 2012), (twelve pages).

Response to Opposition against patent EP2185937 (dated Aug. 24, 2012), (seven pages).

Zenilman et al., "Comparions of reg I and reg III Levels During Acute Pancreatitis in the Rat," Annals of Surger, vol. 323, No. 5, 2000, pp. 646-652.

Blutt et al., "Rotavirus: to the gut and beyond!," Current Opinion in Gastroenterology, Jan. 2007, vol. 23, pp. 39-43.

* cited by examiner

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Forward primer for PSP/reg 1 alpha

<400> SEQUENCE: 1
gaaaagacaa gaggcccaga cagagtt                                        27

<210> SEQ ID NO 2
<211> LENGTH: 31
<212> TYPE: DNA
<213> ORGANISM: Artificial Sequence
<220> FEATURE:
<223> OTHER INFORMATION: Elongation primer for PSP/reg 1 alpha

<400> SEQUENCE: 2
gtatctctcg agaaaagaca agaggcccag a                                   31

<210> SEQ ID NO 3
<211> LENGTH: 21
<212> TYPE: DNA
<213> ORGANISM: Artificial Sequence
<220> FEATURE:
<223> OTHER INFORMATION: Reverse primer for PSP/reg 1 alpha

<400> SEQUENCE: 3 ctagttttg aacttgcata c                                               21

<210> SEQ ID NO 4
<211> LENGTH: 28
<212> TYPE: DNA
<213> ORGANISM: Artificial Sequence
<220> FEATURE:
<223> OTHER INFORMATION: Forward primer for PSP/reg 1 alpha

<400> SEQUENCE: 4
gaaaagacag gagtcccaga cagagctg                                       28

```
<210> SEQ ID NO 5
<211> LENGTH: 32
<212> TYPE: DNA
<213> ORGANISM: Artificial Sequence
<220> FEATURE:
<223> OTHER INFORMATION: Elongation primer for PSP/reg 1 alpha

<400> SEQUENCE: 5
gtatctctcg agaaaagaca ggagtcccag ac                                   32

<210> SEQ ID NO 6
<211> LENGTH: 37
<212> TYPE: DNA
<213> ORGANISM: Artificial Sequence
<220> FEATURE:
<223> OTHER INFORMATION: Reverse primer for PSP/reg 1 beta

<400> SEQUENCE: 6
atctgcagtc tagaattctg caggaccagt tctagac                              37
```

METHOD FOR ASSAYING SEPSIS IN HUMANS

CROSS REFERENCE TO RELATED APPLICATIONS

This is a continuation application claiming benefit of U.S. application Ser. No. 12/676,650 filed Sep. 2, 2008, which is incorporated herein by reference in its entirety and which is U.S. national stage of International application no. PCT/EP2008/007158, filed Sep. 2, 2008 designating the United States and which claims priority to European application no. 07017539.3, filed Sep. 7, 2007.

REFERENCE TO SEQUENCE LISTING

The Sequence Listing submitted herewith as a text file named "3023-122CON-Sequence-Listing," created on Mar. 29, 2013, and having a size of 1594 bytes is hereby incorporated by reference pursuant to 37 C.F.R.1.52(e)(5).

FIELD OF THE INVENTION

The present invention relates to a method of prediction and/or diagnosis of a systematic infection in human, in particular for prediction of the development of sepsis, based on the level of pancreatic stone protein/regenerating protein (PSP/reg) in body fluids, and to an assay kit.

BACKGROUND OF THE INVENTION

Systemic responses to severe trauma include a number of parameters affecting innate immunity, inflammatory reactions and cellular activities. Severe trauma patients may have a benign outcome with no infection while others suffer from infections or sepsis. Sepsis is associated with multiple organ failure and a high mortality. Among the most commonly used markers for diagnosis of sepsis are leukocyte counts, C-reactive protein and procalcitonin. The latter are two proteins highly induced after trauma, yet without any known function. In addition, cytokines such as IL-6, IL-8 and IL-18 are employed to monitor patients. However, none of the above mentioned markers serves as a predictive indicator for infections including sepsis, hence treatment may lag behind the onset of sepsis.

In animal pilot experiments, it has been shown that a pancreatic protein is induced due to handling stress, even in the absence of pancreatic tissue damage (R. Graf et al., J Surg Res 2002, 195:136-144). This protein, pancreatic stone protein/regenerating protein (PSP/reg) belongs to a family of lectin binding proteins. Under conditions of acute or chronic pancreatitis, it is highly up-regulated and may appear in the serum. Since the regulation of this protein is not purely restricted to diet induced secretion like other zymogens, it may appear elevated in other conditions, e.g. during pancreatitis. Thus far, the protein has been studied predominantly in the pancreas. It is also synthesized in PANETH cells of the small intestine and the fundic cells of the stomach. The function of PSP/reg is still highly debated, but it is generally assumed that it is involved in promoting cell proliferation during regenerative processes (Y. Kinoshita et al., J. Gastroenterol 2004, 39:507-513).

Several efforts have been made to establish PSP/reg as a disease marker. So far, it has not been possible to establish a correlation of serum values with a specific disease entity since serum levels are raised in various gastrointestinal diseases Y (Satomura et al., J Gastroenterol 1995, 30:643-650).

SUMMARY OF THE INVENTION

The present invention relates to a method of prediction and/or diagnosis of a systemic infection in humans, in particular for prediction of the development of sepsis, wherein the level of pancreatic stone protein/regenerating protein (PSP/reg) is determined in body fluid sample, and a high level is indicative of the development of sepsis at early stages of the disease. In addition, the present invention relates to a method of determination of PSP/reg levels in body fluids, and a kit of parts for such a method.

Patients were retrospectively categorized: no infection (open boxes, n=14), patients with infection (lightly hatched boxes, n=22), patients with sepsis (darkly hatched boxes, n=27). CRP values ($\log_{10}$ ng/mL) of the three groups are plotted as box plots with the mean and the 95% confidence interval. d=days after trauma. Statistical analysis was performed using multivariate analysis; p=significance, *=p values for sepsis vs. no infection.

Figure 2:
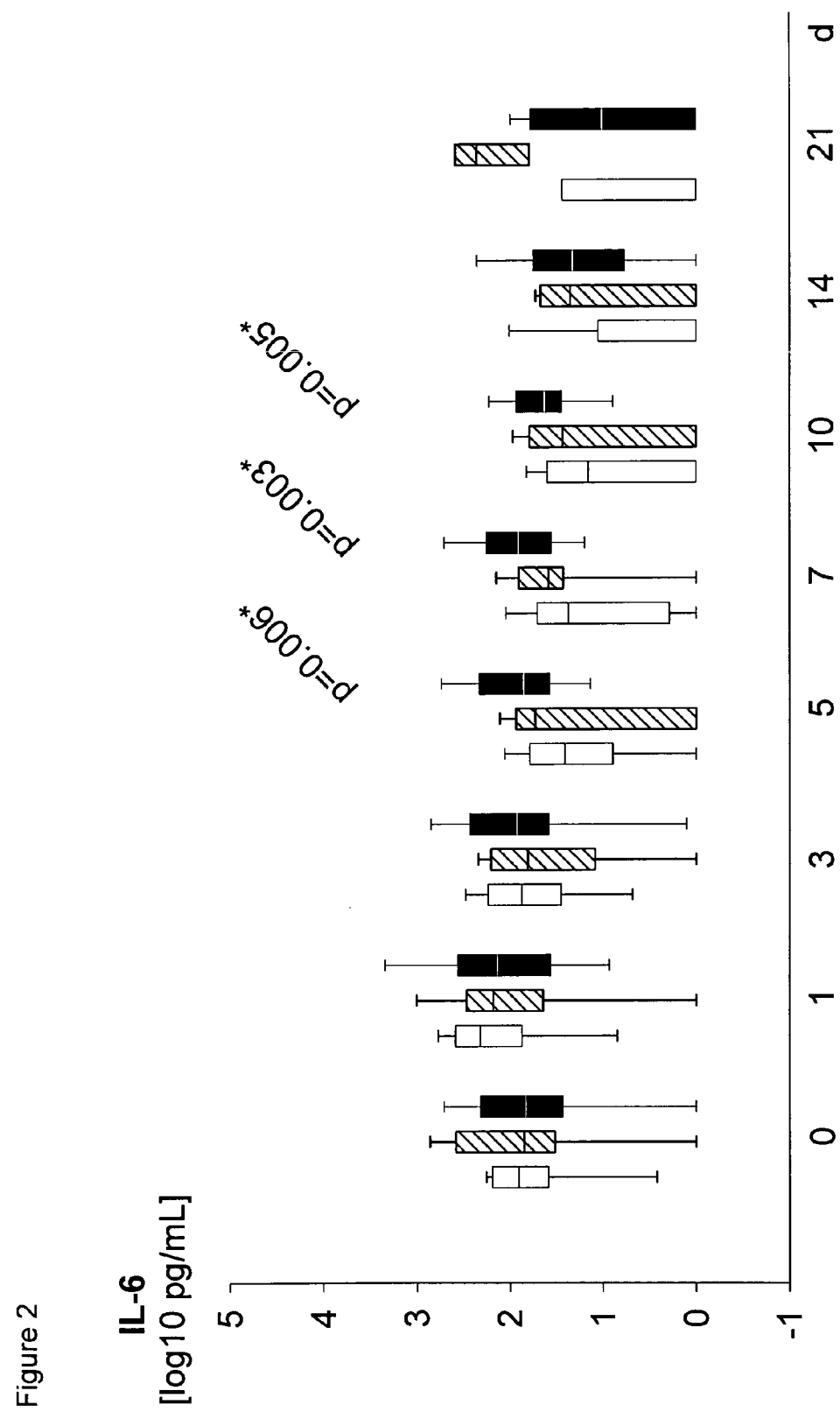

FIG. 2: Determination of IL-6 values in sera of patients after admission to the hospital with a severe trauma.

Figure 1:
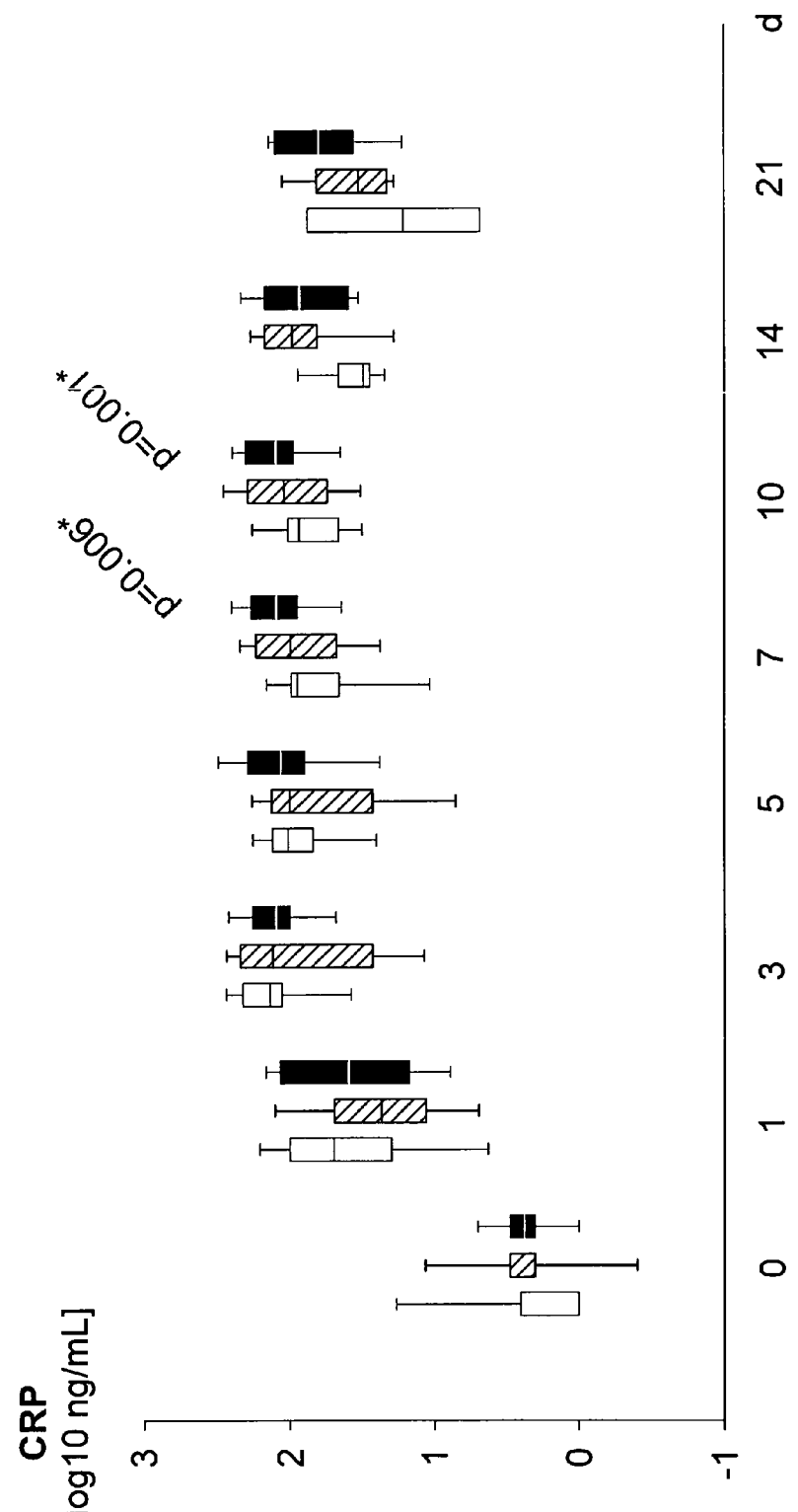
FIG. 1: Determination of C-reactive protein (CRP) values in sera of patients after admission to the hospital with a severe trauma.

Patient categorization and presentation of IL-6 values ($\log_{10}$ pg/mL) in a box blot as for CRP values in FIG. 1.

Figure 3:
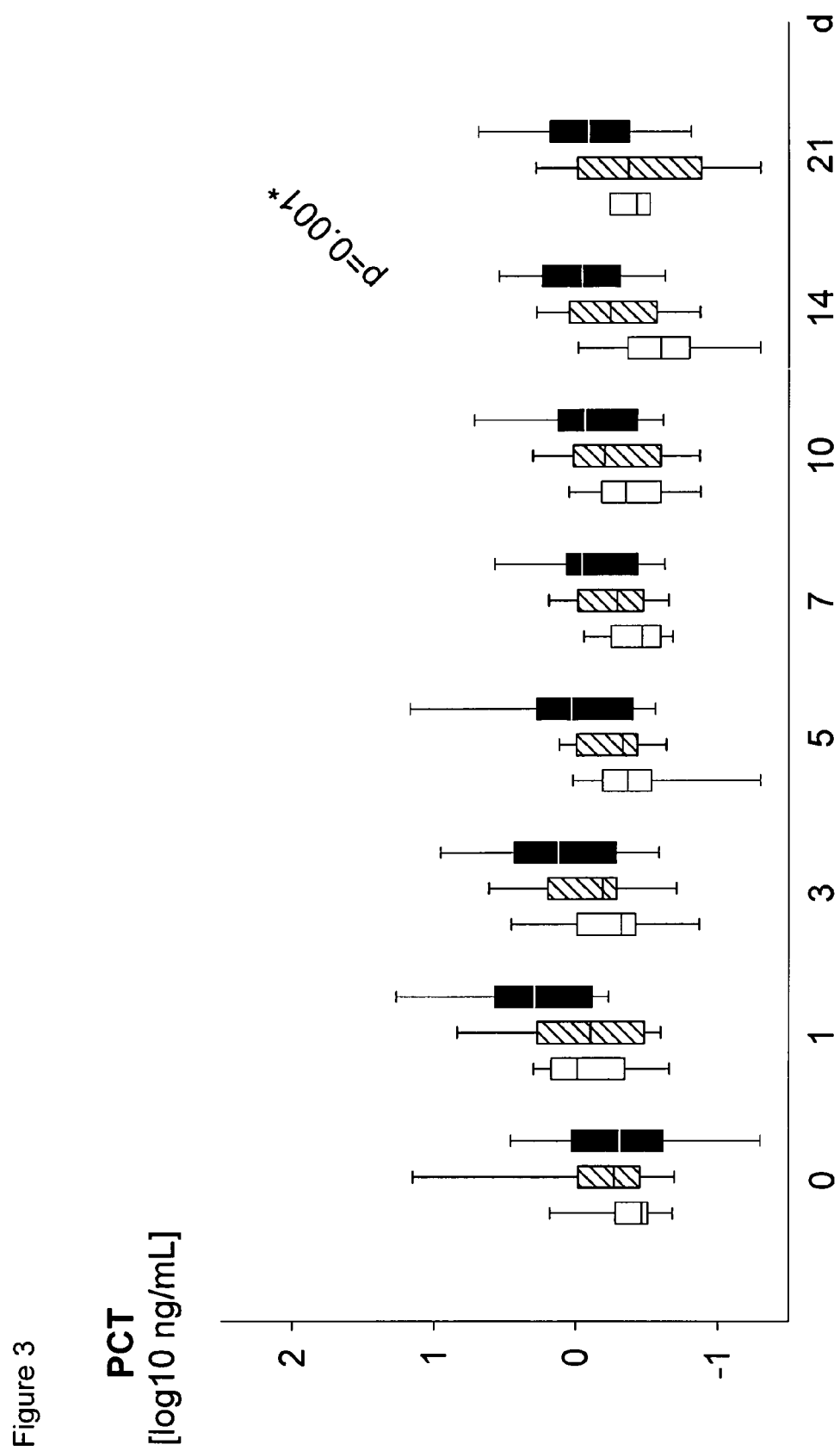

FIG. 3: Determination of procalcitonin (PCT) values in sera of patients after admission to the hospital with a severe trauma.

Patient categorization and presentation of PCT values ($\log_{10}$ ng/mL) in a box blot as for CRP values in FIG. 1.

Figure 4:
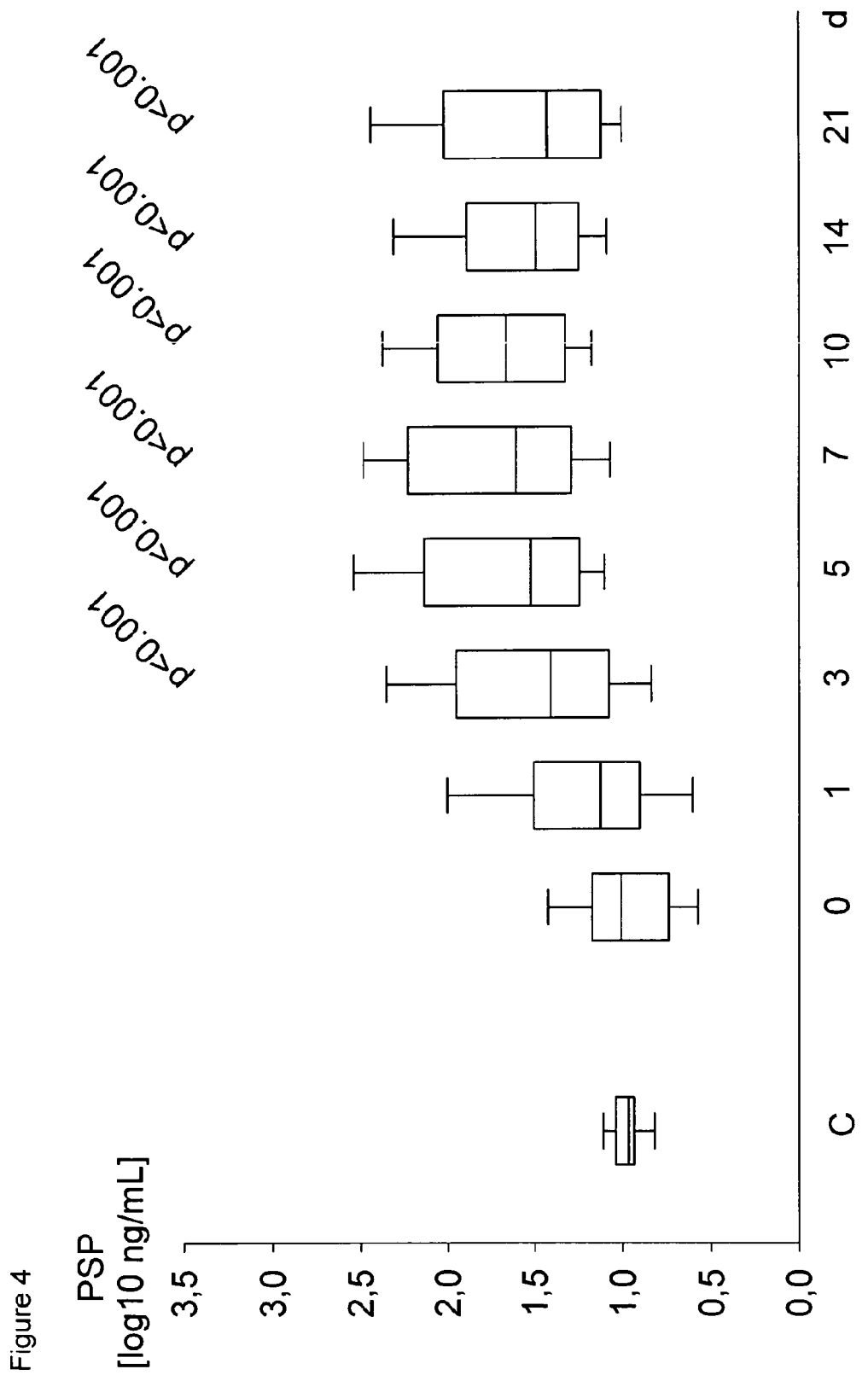

FIG. 4: Determination of pancreatic stone protein/regenerating protein (PSP)

Temporal profile of PSP/reg after a trauma at day 0. All values were combined for each time point. C (=control) indicates value for healthy subjects. d=days after trauma.

FIG. 5: Determination of PSP/reg values in sera of patients after admission to the hospital with a severe trauma.

Figure 5A:
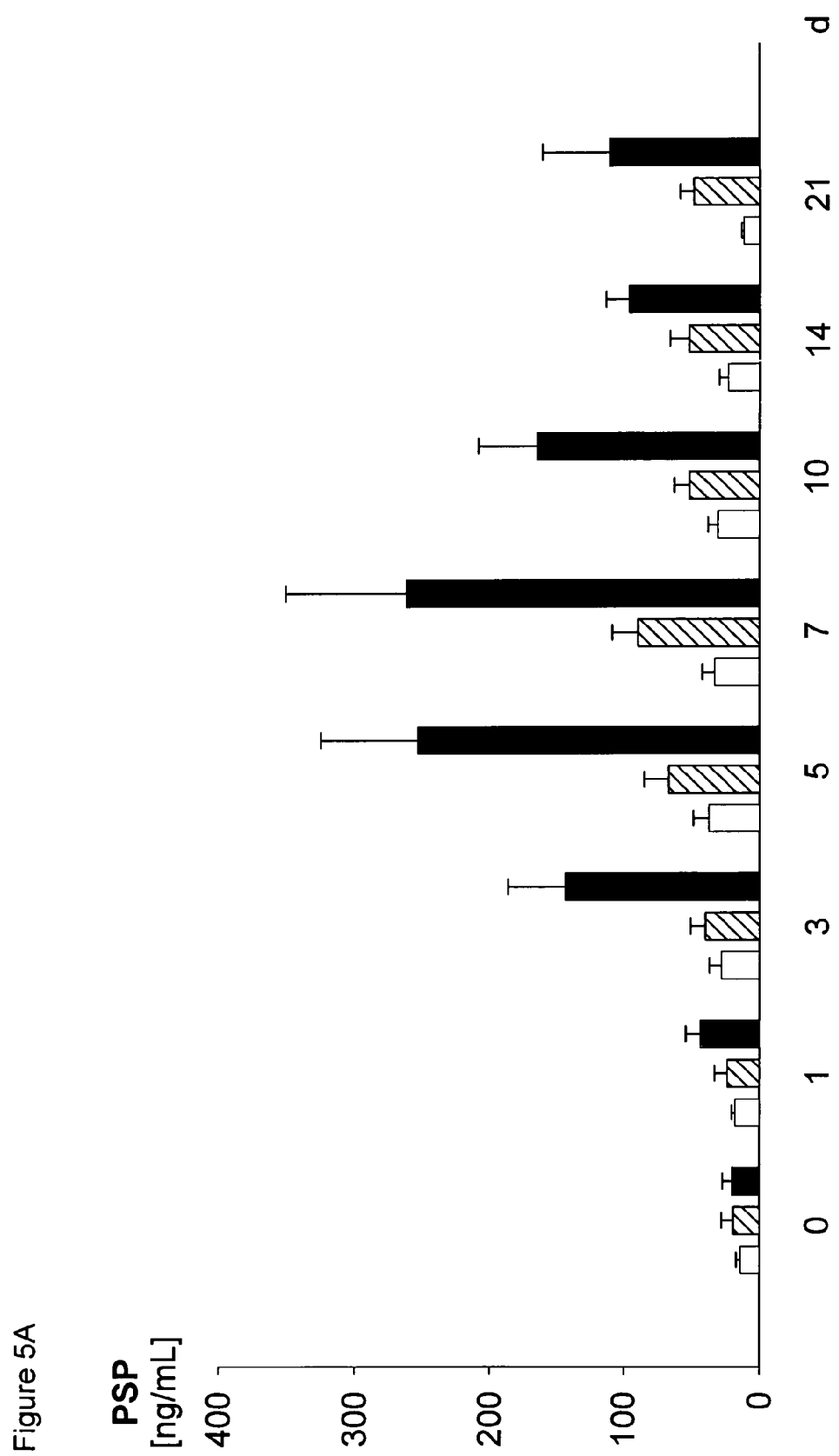

FIG. 5A: Patient categorization and meaning of open, lightly hatched and darkly hatched boxes as for CRP values in FIG. 1. PSP/reg values (ng/mL) of the three groups are plotted as mean+/−SEM. d=days after trauma.

Figure 5B:
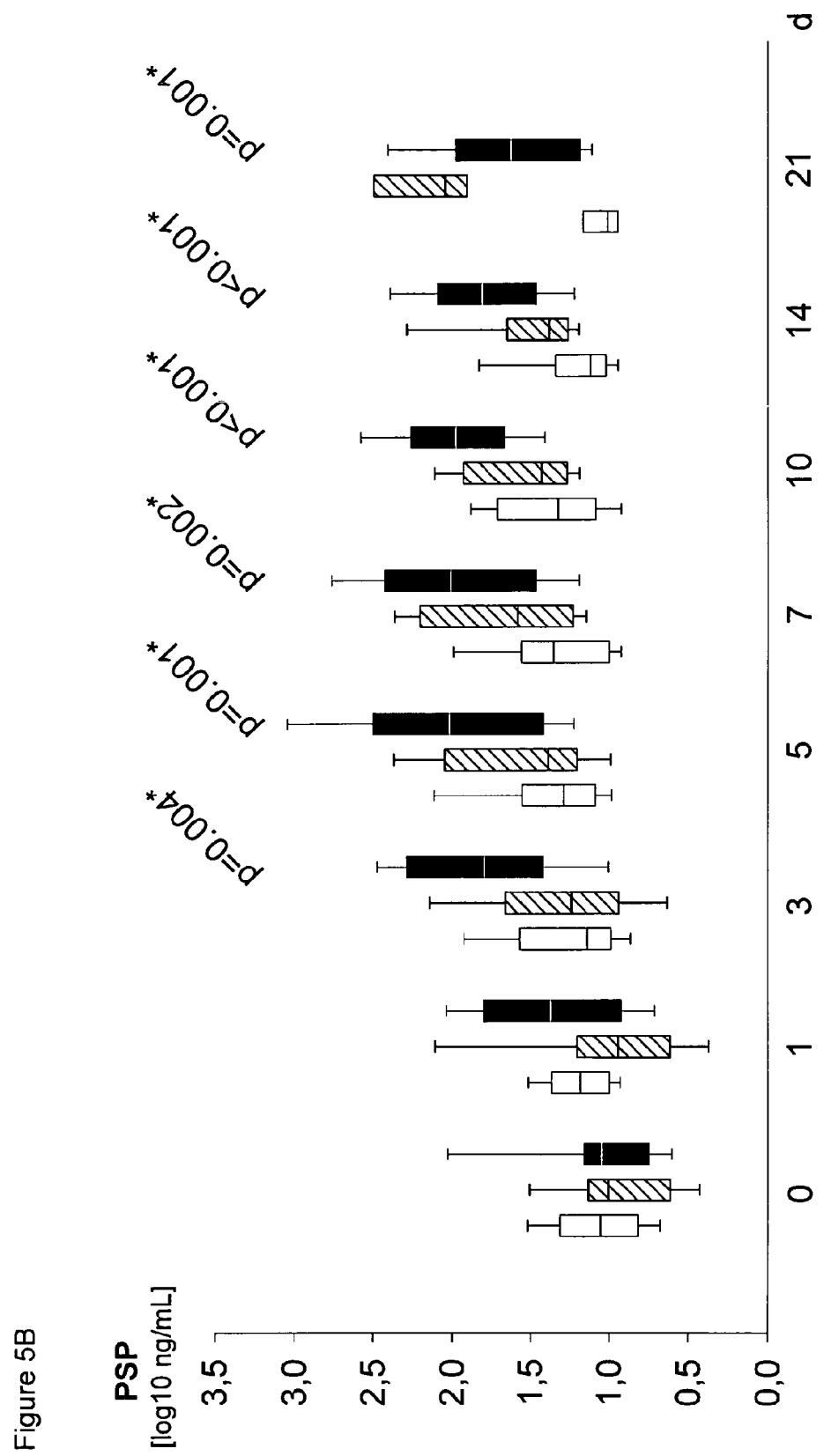

FIG. 5B: Patient categorization and presentation of PSP/reg values (ng/mL) in a box blot as for CRP values in FIG. 1. p=significance, *=p values for sepsis vs. no infection.

DETAILED DESCRIPTION OF THE INVENTION

The present invention relates to a method of prediction and/or diagnosis of a systemic infection in humans, in particular for prediction of the development of sepsis, wherein the level of pancreatic stone protein/regenerating protein (PSP/reg) is determined in a body fluid sample, e.g. serum, and a high level is indicative of the development of sepsis at early stages of the disease.

Other body fluids than serum useful for determination of PSP/reg levels are e.g. whole blood, urine, sputum, cerebrospinal fluid, tear fluid, sweat, milk, or extracts from solid tissue or from fecal matter.

The PSP/reg level indicative for development of posttraumatic sepsis is dependent on the body fluid chosen for the determination. For blood serum this level is 60 to 80 ng/ml on days 3, 4 or 5. Hence, more specifically, the invention relates to a method of prediction and/or diagnosis of the development of sepsis, wherein the level of pancreatic stone protein/regenerating protein (PSP/reg) is determined in serum, and a level of 60 ng/ml or more, in particular a level of 80 ng/ml or more, on days 3, 4 or 5 is indicative of the development of sepsis.

Any known method may be used for the determination of the level of PSP/reg in body fluids. Methods considered are e.g. ELISA, RIA, EIA, mass spectrometry, or microarray analysis. Such methods when used for diagnosis of systemic infection, e.g. sepsis, are a further object of the invention.

A preferred method for the determination of PSP/reg in human body fluids, e.g. serum, is an ELISA. In one embodiment of the invention, the PSP/reg ELISA consists of a sandwich array: Conventional microtiter plates are coated with one type of antibody ("first" antibody"), e.g. a guinea pig polyclonal antibody, directed against PSP/reg. The plates are then blocked and the sample or standard is loaded. After the incubation, a different type of antibody ("second" antibody) against PSP/reg is applied, e.g. a polyclonal rabbit antibody. A third antibody detecting the particular type of the "second" antibody, e.g. a anti-rabbit antibody, conjugated with a suitable label, e.g. an enzyme for chromogenic detection, is then added. Finally the plate is developed with a substrate for the label in order to detect and quantify the label, being a measure for the presence and amount of PSP/reg. If the label is an enzyme for chromogenic detection, the substrate is a colour-generating substrate of the conjugated enzyme. The colour reaction is then detected in a microplate reader and compared to standards.

Suitable pairs of antibodies ("first" and "second" antibody) are any combination of guinea pig, rat, mouse, rabbit, goat, chicken, donkey or horse. Preferred are polyclonal antibodies, but it is also possible to use monoclonal antibodies or antibody fragments. Suitable labels are chromogenic labels, i.e. enzymes which can be used to convert a substrate to a detectable coloured or fluorescent compound, spectroscopic labels, e.g. fluorescent labels or labels presenting a visible colour, affinity labels which may be developed by a further compound specific for the label and allowing easy detection and quantification, or any other label used in standard ELISA.

Other preferred methods of PSP/reg detection are radioimmunoassay or competitive immunoassay using a single antibody and chemiluminescence detection on automated commercial analytical robots. Microparticle enhanced fluorescence, fluorescence polarized methodologies, or mass spectrometry may also be used. Detection devices, e.g. microarrays, are useful components as readout systems for PSP/reg.

The invention further relates to a kit of parts for the determination of PSP/reg for diagnosis/prediction of systemic infection, for example comprising apparatus, reagents and standard solutions of PSP/reg. Apparatus considered are e.g. microtiter plates for ELISA, pre-coated ELISA plates, and plate covers. Reagents are those reagents particularly developed and designed for the detection of PSP/reg. Standard solutions of PSP/reg preferably contain PSP/reg synthesized according to the directions hereinbelow. The kit of parts may contain further hardware, such as pipettes, solutions such as buffers, blocking solutions and the like, filters, colour tables and directions for use.

PSP/reg is a protein expressed in the pancreas and the intestine. It can be cloned from pancreatic mRNA and subcloned into a yeast expression vector. The protein can then be expressed under the control of ADH. A suitable expression medium may comprise methanol to induce and maintain the secretion of PSP/reg. PSP/reg is preferably purified using SP-Sepharose-cellulose by a pH and salt gradient. Such purified PSP/reg is used to prepare standard solutions for comparison with PSP/reg levels in body fluids. Polyclonal antibodies against the protein may be obtained from mice, rats, rabbits, goats, chicken, donkey, horses and guinea pigs or other suitable animals using standard methods.

The reason for the increase of PSP/reg in blood serum during early development stages of sepsis is not entirely clear. In rat pilot experiments an increase in PSP/reg synthesis in the absence of pancreatic damage was observed, and there was evidence that significant traumatic damage to other organs leads to an increase in blood levels of PSP/reg. For further studies a set of human patients with severe trauma but apparent absence of pancreatic damage was chosen (see Examples). The appearance of PSP/reg in blood serum would imply an altered pathway, diverting the protein from pancreatic juice into the blood. It has also been shown that members of the lectin binding family (e.g. pancreatitis-associated protein) are inducible by cytokines. There is a strong and concerted action of cytokines after trauma. The complexity of the cytokine response, with many different cytokines being released, is not understood. Thus it is likely that PSP/reg reacts to cytokines that are raised under condition of systemic stress or trauma. In contrast, other pancreatic enzymes, e.g. amylase and lipase, appear not to be regulated by cytokines, their appearance in the blood being a result of diversion only. The PSP/reg level in blood serum is now proven to be a reliable indicator of sepsis. The increase of PSP/reg in blood might imply a specific stress response.

It is shown that unlike other indicators of inflammation, the level of PSP/reg is highly increased in patients during or before clinical signs of sepsis are apparent. The detection and quantification of serum PSP/reg is accomplished e.g. by a sandwich ELISA with a limit of detection of less than 100 pg/ml. Normal serum values are between 5 and 15 ng/ml. Patients with a severe trauma develop sepsis between day 7 and 10 after the accident causing the trauma. The serum values correlate with the severity of sepsis. They may reach over 200 ng/ml. Before clinical signs of sepsis are available, PSP/reg values start to increase at day 3 to day 5 and reach values above 60-80 ng/ml. These values allow to predict whether a patient will develop sepsis and hence the need for intensive treatment including costly antibiotic treatment and a stay in the intensive care unit. Compared to commercially available diagnostic assays, the PSP/reg ELISA is significantly better in monitoring putative septic patients.

EXAMPLES

Isolation and Subcloning of PSP/reg

In order to obtain cDNA for the production of PSP/reg specific antibodies, such cDNA is prepared by reverse transcription of pancreatic mRNA using state of the art laboratory methods. A PCR reaction using primers specific for the sequence coding for PSP/reg and selectively amplifying PSP/reg cDNA is performed. The PCR reaction is then repeated with the elongation primer to add a sequence specific for insertion into the Pichia pastoris transfection vector. The primer is designed to fuse the coding region of the signal peptide of the alpha-mating factor with a KEX2 site and the coding region of the mature human PSP/reg. Subcloning into the Pichia pastoris vector is a two-step procedure. First the PCR product is ligated into the pCR2.1 vector (Invitrogen, TAcloning) and the sequence verified. Then the PCR product is cleaved by XhoI/NotI restriction digestion and ligated into transfer vector pPIC9 (Invitrogen). The Pichia pastoris strain KM71 (Invitrogen) is transformed and the most productive clone is selected for expansion and production of recombinant protein.

Primers used for PCR Amplification and Subcloning

```
Human PSP/reg/reg1 alpha
Forward primers
                                        (SEQ ID NO: 1)
5' GAAAAGACAAGAGGCCCAGACAGAGTT 3'

(SEQ ID NO: 2)
5' GTATCTCTCGAGAAAAGACAAGAGGCCCAGA 3'
(elongation)

Reverse
                                        (SEQ ID NO: 3)
5' CTAGTTTTTGAACTTGCATAC 3'

Human PSP/reg/reg1 beta
Forward primers
                                        (SEQ ID NO: 4)
5' GAAAAGACAGGAGTCCCAGACAGAGCTG 3'

(SEQ ID NO: 5)
5' GTATCTCTCGAGAAAAGACAGGAGTCCCAGAC 3'
(elongation)

Reverse primer
                                        (SEQ ID NO: 6)
5' ATCTGCAGTCTAGAATTCTGCAGGACCAGTTCTAGAC 3'
```

Large Scale Expression of Protein

Using a single colony, 25 ml of BMG (buffered minimal glycerol, 100 mM potassium phosphate pH 6.0, 1.34% yeast nitrogen base, $4\times10^{-5}$% biotin, 1% glycerol) is inoculated in a 250 ml baffled flask and grown at 29° C. in a shaking incubator (300 rpm) overnight. 10 ml of this culture is used to inoculate 1 liter of BMG in a 3 liter baffled flask and grown at 29° C. (300 rpm) overnight. The cells are harvested by centrifugation at 1500-3000×g for 5 minutes at room temperature. Expression is induced by resuspending the cells in ⅕ volume (200 ml) of BMM (buffered minimum methanol, BMG in which glycerol is replaced by 0.5% methanol) in the same baffled flask. 100% methanol is added to achieve a concentration of 0.5% (1 ml) every 24 hrs until optimal time of induction is reached. The cells are harvested by centrifugation at 1500-3000×g at room temperature. The medium supernatant is collected and frozen until purification of the peptide.

The polypeptide is purified from media supernatants. Media supernatants are diluted 1:3 with distilled water. The pH is adjusted to pH 3.5 with HCl. The medium supernatant is then applied to a SP-Sepharose column and eluted by a salt and pH gradient (10 mM LiCl, 50 mM MES, pH 5.3 starting buffer, 2 M LiCl, 50 mM MES, pH 6.3 end buffer). Fractions are collected and analyzed by SDS-gel electrophoresis. The fractions with the highest and purest protein contents are combined and dialyzed against 10 mM HEPES pH 7.5. The sequence of the polypeptide is verified by N-terminal sequencing and the concentration is assessed by amino acid analysis.

PSP/reg ELISA

In order to determine total PSP/reg, a sandwich ELISA may be used on the basis of a guinea pig antiserum raised against recombinant human PSP/reg and a rabbit antiserum against the same protein. To improve the specificity and sensitivity of the rabbit antibody, IgGs are purified by absorption on a column of protein A beads (HiTrap®, Pharmacia): A HiTrap® column is equilibrated with 200 mM $NaH_2PO_4/Na_2HPO_4$ at pH 7. The rabbit antiserum is pH-adjusted with the same buffer solution (final concentration 20 mM) and then loaded onto the column, which is afterwards washed with 100 mM and 10 mM Tris/HCl pH 8 consecutively. The IgG fraction is eluted with 0.1 M citric acid pH 3. The eluted fractions are immediately neutralized with 1 M Tris/HCl pH 8.9.

96-well microtiter plates (Costar EIA plates, flat bottom, high binding) are coated over night at 4° C. with guinea pig anti-rat PSP/reg IgG fraction, diluted 1:500 in TBS (100 μl/well). After a washing step, the plate is blocked with 150 μl 1% BSA/TBS for one hour, which is afterwards replaced by 100 μl of different standard concentrations of recombinant human PSP/reg (0, 0.1, 0.5, 1.0, 1.5, 2.5, 3.5, or 5.0 ng/ml) or 100 μl samples of diluted sample. Samples and standards are loaded in duplicates and incubated for 1 hr at room temperature. After repeated washing, the plate is incubated for 1 hr with 100 μl rabbit anti-rat PSP/reg IgG, diluted 1:500. Another washing step follows before a 30 min incubation with 100 μl of a commercially available mouse monoclonal anti-rabbit IgG antibody is started (mouse anti-rabbit alkaline phosphatase conjugated, IgG fraction, diluted 1:1000; purchased from Sigma). The plate is then washed again, and a soluble phosphatase substrate, p-nitrophenyl phosphate disodium (Sigma 104® tablets), added in alkaline phosphatase buffer (100 mM Tris/HCl pH 9.5, 100 mM NaCl, 0.8 mM $MgCl_2$). After an incubation period of about 20 min optical density (OD) at 405 nm is measured in an MRX microplate reader (Dynatech Laboratories).

All dilutions (except coating antibodies) are prepared in 1% BSA/TBS. All incubations at room temperature are carried out on a rotational ELISA plate shaker (Titramax 100, Heidolph, Bioblock Scientific). All washing steps are performed with TBS/Tween 20 (0.05%, v/v), using an automatic microtiter plate washer (MRW, Dynatech Laboratories). Recovery rates of recombinant PSP/reg into diluted serum from a healthy volunteer is as follows: 71% at 1:10, 118% at 1:20 and 95% at 1:40 dilution. Intraplate and interplate variance is less than 5% and 10%, respectively for concentrations within the range of the standard (between 0.1 and 3.5 ng/ml).

The test is established with recombinant human PSP/reg1 alpha. Recombinant PSP/reg1 beta, the second isoform, was made using the same technique. PSP/reg 1 beta is recognized equally well by the ELISA. Therefore, the ELISA is specific for the known PSP/reg family of proteins.

Test Patients for Proof of Principle

The study population included 63 injured patients who were admitted to the Division of Trauma Surgery (level I trauma center), University Hospital Zurich, in a time period from January 2002 to September 2003. Inclusion criteria were an injury severity score (ISS)>16 points, patient age>16 years, less than four hours between accident and hospital admission, and surveillance on the intensive care unit (ICU) with a survival of more than five days. Patients with a pancreatic injury were excluded. All patients were treated according to the advanced trauma life support (ATLS) guidelines and a standard trauma protocol. In brief, after control of airway, ventilation, and monitoring of cardiovascular functions, life-saving procedures including decompression of body cavities, control of hemorrhage and contamination were carried out. This was followed by radical wound debridement, decompression of compartments, and primary stabilization of major fractures mostly through external fixation ("day one surgery"). Thereafter, patients were transferred to the ICU for restoration of organ functions. Of note, all patients received enteral nutrition within 24 hours after trauma to maintain normal intestinal flora and bowel mucosa. Antibiotics were used, if a septic focus was verified by a positive bacterial culture. In addition, for open fractures standard antibiotics are applied for five days and a single shot of a cephalosporin was given as prophylaxis for osteosynthesis of fractures.

Table 1 summarizes demographic data and injury scores at the day of admission. The severity of injury and gender distribution were very similar.

TABLE 1

Demographic data of enrolled patients

| Parameter | No infection | Infection | Sepsis |
|---|---|---|---|
| Number | 14 | 22 | 27 |
| Age (yr) | 38.6 ± 16.9 | 36.6 ± 15.5 | 37.3 ± 16.0 |
| Males | 11 (78.6%) | 15 (68.2%) | 22 (81.5%) |
| ISS[a] (points) | 34.6 ± 9.3 | 32.2 ± 13.9 | 38.7 ± 15.6 |
| GCS[b] (points) | 8.9 ± 5.2 | 9.2 ± 4.9 | 8.8 ± 5.1 |
| APACHE II[c] (points) | 15.0 ± 6.2 | 13.6 ± 6.6 | 17.0 ± 6.8 |
| ICU[d] (days) | 9.1 ± 5.9 | 16.3 ± 8.2 | 26.6 ± 9.9 |

Mean ± SD. Values in parentheses are percentages.
[a]ISS, injury severity score
[b]GCS, Glasgow coma scale
[c]APACHE II, acute physiology and chronic health evaluation II
[d]ICU, intensive care unit.

Blood Status of Trauma Patients

Patients are retrospectively assigned to three groups depending on their score: a) no infection, b) infection and c) sepsis (Table 2). To demonstrate the course of several parameters used to determine the extent of inflammation and injury, blood leukocyte counts and C-reactive protein were determined. All patients exhibited a strong reduction of blood leukocytes at day one of hospitalization, irrespective of the severity group. Leukocytes gradually increase to normal with the exception of septic patients which reach a significantly higher leukocyte count of $18 \times 10^6$/L at day 10. Concurrent determination of C-reactive protein (CRP) indicate a gradual increase from low levels at admission to about 150 ng/ml at day three in all groups (FIG. 1). Although the non-infected group has consistently lower levels than the other groups, there is no obvious pattern that distinguishes the three patient groups. Thus between day 5 and day 7 and between day 14 and 21, septic patients exhibit a higher CRP than non-septic patients, the difference being less than a factor of two.

TABLE 2

Injury pattern and posttraumatic course of enrolled patients

| Parameter | No infection (n = 14) | Infection (n = 22) | Sepsis (n = 27) |
|---|---|---|---|
| Head (AIS[a], points) | 85.7% (3.4) | 86.4% (3.7) | 70.4% (4.1) |
| Thorax (AIS[a]; points) | 78.6% (3.0) | 36.4% (3.3) | 63.0% (3.5) |
| Abdomen (AIS[a]; points) | 50.0% (3.7) | 36.4% (3.8) | 44.4% (4.1) |
| Extremities (AIS[a]; points) | 57.1% (3.0) | 68.2% (2.3) | 63.0% (2.5) |
| Pelvis (AIS[a]; points) | 21.4% (3.0) | 22.7% (2.6) | 18.5% (2.8) |
| Spine (AIS[a]; points) | 42.9% (2.8) | 36.4% (2.5) | 25.9% (2.9) |
| No SIRS[b] | 2 (14.3%) | — | — |
| SIRS 2[b] | 5 (35.7%) | 2 (9.1%) | — |
| SIRS 3/4[b] | 7 (50.0%) | 20 (90.9%) | — |
| Sepsis | — | — | 27 (100%) |
| Mortality | 2 (14.3%) | 2 (9.1%) | 5 (18.5%) |

[a] AIS, abbreviated injury scale
[b] SIRS, systemic inflammatory response syndrome Determination of Standard Indicators of Inflammation in Trauma Patients To determine whether commonly used indicators of inflammation, e.g. IL-6 (FIG. 2) and procalcitonin (PCT, FIG. 3), could distinguish between the three severity groups, blood levels of these proteins were measured during the whole course of the hospital stay. IL-6 immediately increased prostraumatically reaching the highest levels at day 1. During the first two days the three severity groups are different, with the septic group (1200 pg/ml) and the infected group (600 pg/ml) higher than the non-infected group. The statistics do not indicate significance due to the high variability of the data while at day 5-10 there was a difference. Although there is a slight increase during the time of sepsis (350 pg/ml) these levels are low in comparison to the first day of hospitalization.

PCT was clearly increased 20-fold in the septic patient group prior to and during sepsis, while the other groups remain at levels around 0.5-2 ng/ml (FIG. 3). The maximal increase in PCT was 25 fold versus healthy subjects. The statistics do not indicate significant differences due to the high variation in the sample.

PSP/reg is Upregulated Posttraumatically

PSP/reg is synthesized predominantly in the pancreas and in the intestine. In response to a local tissue injury it is highly upregulated. In the absence of pancreatic tissue injury, PSP/reg is not expected to be up-regulated. However, polytrauma causes a release of cytokines that may affect the expression and secretion of PSP/reg. Therefore, it was tested whether these proteins are increased in patients with severe trauma that had no pancreatic injury. The combined data of all patients after polytrauma indicate an increase at day one that becomes significant at day three, compared to day zero as well as compared to healthy subjects (FIG. 4).

Thus, pancreatic stone protein is slightly increased after a polytrauma. The data were then analyzed using stratification assigned to patients without infection, patients with infection and patients with sepsis. PSP/reg values in patients without an infection are slightly increased with a peak at day 7-10 (FIGS. 5A, 5B). In patients with polytrauma that exhibit infection, there is a further increase. Finally, polytraumatic patients exhibiting sepsis show a large increase in serum PSP/reg.

The increase starts several days before clinical criteria of sepsis are fulfilled. PSP/reg highly correlates with sepsis. At day 3, when patients are not septic yet the average level of PSP in blood increases significantly to over 100 ng/ml and reaches about 20-fold during the time of sepsis (FIGS. 5A, 5B, day 5-10).

The early increase of PSP/reg in patients with sepsis can therefore be used as a serum marker to predict sepsis. Therefore the specificity, the positive and the negative predictive values are summarized for three potential cut-off values e.g. 30, 60 and 80 ng/ml at day three and five. The specificity is around 80 percent for cut-off values of 60 and 80 ng/ml. The positive and negative predictive values above are also between 60 and 80% indicating that patients can be identified by this method early on.

TABLE 3

Sensitivity, specificity, and positive and negative predictive values for three cut off points of PSP serum levels for patients with sepsis compared with patients without infectious complications or local infections. The two groups non-infection were compared with the septic group. The infectious group is not included.

|  | 30 ng/mL | 60 ng/mL | 80 ng/mL |
|---|---|---|---|
| Day 3 |  |  |  |
| Sensitiviy (%) | 70.4 | 55.5 | 40.7 |
| Specificity (%) | 72.2 | 83.3 | 83.3 |
| Positive predictive value (%) | 65.5 | 71.4 | 64.7 |
| Negative predictive value (%) | 76.5 | 71.4 | 65.2 |
| Day 5 |  |  |  |
| Sensitiviy (%) | 74.1 | 63.0 | 51.9 |
| Specificity (%) | 66.7 | 75.0 | 77.7 |
| Positive predictive value (%) | 62.5 | 65.4 | 63.6 |
| Negative predictive value (%) | 77.4 | 73.0 | 68.3 |

The analysis is based on PSP serum values obtained on day 3 or day 5 after trauma.

What we claim is:

1. A method of quantifying pancreatic stone protein/regenerating protein (PSP/reg) in a serum sample comprising:
   (a) obtaining the serum sample from a human who suffered from trauma 3, 4 or 5 days after said trauma, wherein the human did not suffer from pancreatic injury, and
   (b) detecting an increased level of PSP/reg by measuring a level of PSP/reg that is higher than 60 ng/ml in said serum sample, wherein said measuring is performed by contacting the serum sample with an antibody against PSP/reg, and
   (c) treating said human having a level of PSP/reg higher than 60 ng/ml by administering an antibiotic to treat sepsis.

2. The method of claim 1, wherein said human is monitored for sepsis.

3. The method of claim 1, wherein the level of PSP/reg is above 80 ng/ml.

4. The method of claim 1, wherein the level of PSP/reg is detected by ELISA, RIA, EIA, mass spectrometry, or microarray analysis.

5. The method of claim 1, wherein the level of PSP/reg is detected via a sandwich ELISA, comprising:
   providing microtiter plates coated with a first antibody directed against PSP/reg,
   blocking said plates,
   loading the sample onto said plates,
   applying a second antibody against PSP/reg in the sample,
   adding a third antibody that detects the second antibody, wherein said third antibody is conjugated with a label, and
   adding a substrate for the label to detect and quantify the label.

6. The method of claim 5, wherein the label is an enzyme for chromogenic detection and the substrate is a color-generating substrate of the conjugated enzyme.

7. The method of claim 5, wherein the first antibody and the second antibody against PSP/reg in the sample are polyclonal antibodies.

8. The method of claim 1, wherein the binding between said antibody and PSP/reg is detected and said antibody is a polyclonal antibody raised in an animal.

9. The method of claim 8, wherein said antibody is obtained from mice, rats, rabbits, goats, chicken, donkey, horses or guinea pigs.

10. The method of claim 1, wherein a pair of guinea pig, rat, mouse, rabbit, goat, chicken, donkey or horse antibodies is provided in said detecting PSP/reg and wherein one of said antibodies of said pair is against PSP/reg.

11. The method of claim 1, wherein a single antibody against PSP/reg is provided in said detecting PSP/reg and binding of said single antibody to PSP/reg is detected via chemiluminescence detection on automated commercial analytical robots,
   microparticle enhanced fluorescence,
   fluorescence polarized methodologies,
   or mass spectrometry.

12. The method of claim 1, wherein a single antibody against PSP/reg is provided in said detecting PSP/reg, said single antibody is a guinea pig, rat, mouse, rabbit, goat, chicken, donkey or horse antibody and binding of said single antibody to PSP/reg is detected.

* * * * *